United States Patent [19]
Gavin et al.

[11] Patent Number: 5,800,781
[45] Date of Patent: *Sep. 1, 1998

[54] BLOOD SAMPLING DEVICE

[75] Inventors: Michael Gavin, Warren; Catherine M. Cimini, Somerset; Ming Huang, Milltown; Anthony Kuklo, Jr., Bridgewater, all of N.J.; James A. Mawhirt, Brooklyn, N.Y.; Eduardo Marcelino, Edison; Albert Simone, Fords, both of N.J.

[73] Assignee: International Technidyne Corporation, Edison, N.J.

[*] Notice: The term of this patent shall not extend beyond the expiration date of Pat. No. 5,518,006

[21] Appl. No.: 719,779

[22] Filed: Sep. 25, 1996

Related U.S. Application Data

[62] Division of Ser. No. 617,296, Mar. 18, 1996, Pat. No. 5,591,403, which is a division of Ser. No. 424,063, Apr. 19, 1995, Pat. No. 5,534,226, which is a division of Ser. No. 327,320, Oct. 21, 1994, Pat. No. 5,504,011.

[51] Int. Cl.⁶ ............................................. G01N 33/86
[52] U.S. Cl. ............... 422/73; 422/58; 422/102; 422/104; 606/181; 606/182; 606/183; 128/710; 128/763; 128/765; 128/770
[58] Field of Search ............... 422/58, 73, 102, 422/104; 606/181–183; 128/760, 763, 770, 765

[56] References Cited

U.S. PATENT DOCUMENTS

| | | | |
|---|---|---|---|
| 1,020,753 | 3/1912 | Ford . | |
| 3,307,392 | 3/1967 | Owen et al. | 73/64.1 |
| 3,486,859 | 12/1969 | Greiner et al. | 23/253 |
| 3,658,480 | 4/1972 | Kane et al. | 23/230 B |
| 3,695,842 | 10/1972 | Mintz | 23/230 R |
| 3,741,197 | 6/1973 | Sanz et al. | 128/2 F |
| 3,836,333 | 9/1974 | Mintz | 23/259 |
| 3,841,307 | 10/1974 | Friedell | 128/2 G |
| 3,890,098 | 6/1975 | Moreno | 23/230 B |
| 3,951,606 | 4/1976 | Moyer et al. | 23/253 R |
| 4,066,829 | 1/1978 | Nair et al. | 536/103 |
| 4,197,734 | 4/1980 | Rosenberg | 73/64.1 |
| 4,360,016 | 11/1982 | Sarrne | 128/763 |
| 4,397,318 | 8/1983 | Burns | 128/763 |
| 4,503,011 | 3/1985 | Hubeau | 422/73 |
| 4,627,445 | 12/1986 | Garcia et al. | 128/770 |
| 4,637,403 | 1/1987 | Garcia et al. | 128/330 |
| 4,653,513 | 3/1987 | Dombrowski | 128/765 |
| 4,659,550 | 4/1987 | Schildknecht | 436/69 |
| 4,690,153 | 9/1987 | Losado et al. | 128/763 |
| 4,725,554 | 2/1988 | Schildknecht | 422/73 |
| 4,756,884 | 7/1988 | Hillman et al. | 422/73 |
| 4,780,418 | 10/1988 | Kratzer | 439/69 |
| 4,787,398 | 11/1988 | Garcia et al. | 128/770 |
| 4,797,369 | 1/1989 | Mintz | 436/69 |
| 4,813,426 | 3/1989 | Haber et al. | 128/763 |
| 4,849,340 | 7/1989 | Oberhardt | 435/13 |

(List continued on next page.)

*Primary Examiner*—Jill Warden
*Assistant Examiner*—Sharidan Carrillo
*Attorney, Agent, or Firm*—Plevy & Associates

[57] ABSTRACT

A portable device for performing coagulation tests on a patient's blood. Blood is first drawn from a patient using a lancet. The blood is then supplied to a disposable cuvette placed within the testing device. The blood is drawn into multiple conduits within the cuvette. Each of the conduits contains a dried or lyophilized activation reagent that is rehydrated by the blood. The blood in each of the conduits is then reciprocally moved across a restricted region until a predetermined degree of coagulation occurs. Since the coagulation time is being monitored in multiple conduits, a representation coagulation time for a given sample can be determined. In at least one of the conduits a normalizing control agent is present. The normalizing control agent counteracts any effects of anticoagulants present in the blood sample, thereby allowing the blood sample to have generally normal coagulation characteristics. The normalized blood is tested simultaneously with the untreated blood to provide a reference value against which the functionality of the test system and the quality of the sample can be judged.

6 Claims, 13 Drawing Sheets

5,800,781

Page 2

U.S. PATENT DOCUMENTS

| | | | |
|---|---|---|---|
| 4,873,993 | 10/1989 | Meserol et al. | 128/760 |
| 4,889,117 | 12/1989 | Stevens | 606/181 |
| 4,920,977 | 5/1990 | Haynes | 128/770 |
| 4,924,879 | 5/1990 | O'Brien | 128/770 |
| 4,963,498 | 10/1990 | Hillman et al. | 436/69 |
| 4,967,763 | 11/1990 | Hugent et al. | 128/763 |
| 4,995,402 | 2/1991 | Smith et al. | 128/771 |
| 5,000,167 | 3/1991 | Sunderland | 128/763 |
| 5,019,351 | 5/1991 | Schulz | 422/99 |
| 5,029,583 | 7/1991 | Meserel et al. | 128/633 |
| 5,039,617 | 8/1991 | McDonald et al. | 436/69 |
| 5,055,557 | 10/1991 | Zimmerman | 530/381 |
| 5,057,141 | 10/1991 | Rodriquez-Kabana et al. | 71/28 |
| 5,091,304 | 2/1992 | Laduca et al. | 435/13 |
| 5,133,730 | 7/1992 | Biro et al. | 606/182 |
| 5,140,161 | 8/1992 | Hillman et al. | 250/341 |
| 5,147,607 | 9/1992 | Mochida | 422/57 |
| 5,154,082 | 10/1992 | Mintz | 73/64.1 |
| 5,163,442 | 11/1992 | Ono | 128/760 |
| 5,238,854 | 8/1993 | Behnk | 436/69 |
| 5,284,624 | 2/1994 | Behnk | 422/102 |
| 5,298,224 | 3/1994 | Plum | 422/73 |
| 5,300,779 | 4/1994 | Hillman et al. | 436/69 |
| 5,302,348 | 4/1994 | Cusack et al. | 422/73 |
| 5,314,441 | 5/1994 | Cusack et al. | 606/182 |
| 5,316,727 | 5/1994 | Suzuki et al. | 422/68.1 |
| 5,350,676 | 9/1994 | Oberhardt et al. | 435/13 |
| 5,366,903 | 11/1994 | Lundsgaerd et al. | 436/165 |
| 5,372,946 | 12/1994 | Cusak et al. | 436/69 |
| 5,504,011 | 4/1996 | Gavin et al. | 436/69 |
| 5,518,006 | 5/1996 | Mawhirt et al. | 128/770 |
| 5,582,184 | 12/1996 | Erickson et al. | 128/763 |
| 5,731,212 | 3/1998 | Gavin et al. | 436/526 |

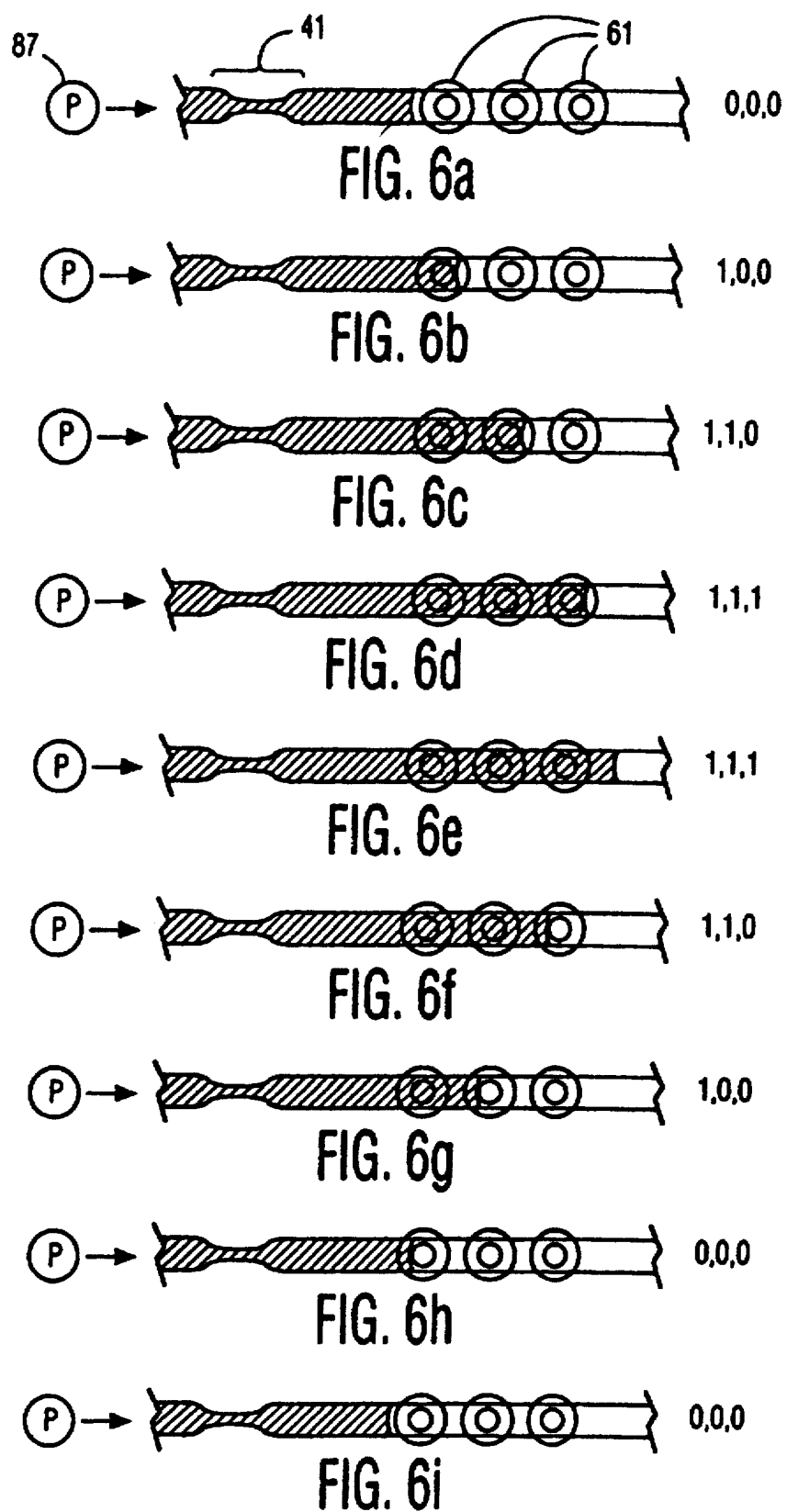

BLOOD SAMPLING DEVICE

This is a Divisional of application Ser. No. 617,296 now U.S. Pat. No. 5,591,403, filed on Mar. 18, 1996 for PORTABLE PROTHROMBIN TEST APPARATUS AND ASSOCIATED METHOD OF PREFORMING A BLOOD COAGULATION TEST which is a divisional of 08/424, 063, filed on Apr. 19, 1995 for PORTABLE TEST APPARATUS AND ASSOCIATED METHOD OF PREFORMING A BLOOD COAGULATION TEST, now U.S. Pat. No. 5,534,226, which is a divisional of 08/327,320, filed on Oct. 21, 1994 for PORTABLE TEST APPARATUS AND ASSOCIATED METHOD OF PREFORMING A BLOOD COAGULATION TEST, now U.S. Pat. No. 5,504,011.

BACKGROUND OF THE INVENTION

1. Field of the Invention

The present invention relates to portable devices for performing blood coagulation tests on blood such as a prothrombin time tests, and the associated methods used to preform such tests.

2. Prior Art Statement

Many people with heart disease, venous thrombosis, history of strokes and the like are prescribed medications to reduce the coagulation characteristic of their blood. A commonly prescribed medication is sodium warfarin isopropanol clathrate, generically known as warfarin and commonly known by the brand name COUMADIN®, produced by DuPont Pharmaceuticals of Wilmington, Del. Warfarin acts to inhibit the synthesis of vitamin K dependent factors. The resultant effect in the body of the patient is a sequential depression of blood Factors VII, IX, X and II. Upon the oral administration of warfarin, the anticoagulation effect generally occurs within 24 hours. However, depending upon the patient, the peak anticoagulant effect may be delayed 72 to 96 hours and its duration may persist for four to five days. Accordingly, it is known that warfarin is a potent drug with a half-life of approximately 2½ days, therefore the effects of warfarin on a patient may become more pronounced as daily maintenance doses overlap. Accordingly, due to the potency of warfarin and its long lasting effects, it is critical that the level of warfarin in a patient be closely monitored. An overdose may cause spontaneous internal bleeding while an underdose would not be an effective anticoagulant, resulting in thrombosis. Additionally, the need for exact blood monitoring is more critical with warfarin than with many other drugs because the relative effectiveness of warfarin is affected by many other prescription and over-the-counter medications that may be taken by a patient using warfarin.

The most common manner of determining the effective amount of warfarin in a patient's blood is to preform a prothrombin time (PT) test. A PT test measures how long a sample of blood takes to clot. As a result, the amount of anticoagulant in the blood can be calculated since the concentration of anticoagulant is directly proportional to the length of time required to form clots the blood sample.

The prior art is replete with various devices and methods for measuring the coagulation time of blood samples. For example, such a method and apparatus is shown in U.S. Pat. No. 5,302,348 to Cusack et al., entitled BLOOD COAGULATION TIME TEST APPARATUS AND METHOD, which issued Apr. 12, 1994 and is assigned to International Technidyne Corporation, the assignee herein. This patent shows a machine that measures the coagulation time of blood placed in disposable cuvettes by pneumatically moving the blood through a single restricted passage in the cuvette.

U.S. Pat. No. 5,154,082 to Michael Mintz, entitled MICROPROCESSOR-CONTROLLED APPARATUS AND METHOD FOR DETECTING THE COAGULATION OF BLOOD, issued Oct. 13, 1992 and assigned to the assignee herein, shows a device that measures blood coagulation by its effect on a ferromagnetic member in an electromagnetic field.

U.S. Pat. No. 4,797,369 which issued on Jan. 10, 1989 entitled METHOD AND APPARATUS FOR DETECTING A BLOOD CLOT to Michael Mintz, and assigned to the assignee herein, shows the technique for measuring clot time whereby a sample of whole blood or blood plasma is dispersed into two or more zones. The zones are separated and brought together repeatedly, such that the blood sample is divided into multiple parts each associated with a zone. The parts are then rejoined into a single part and the process of separation and joining continues. During the process, a liquid bridge between the separated parties is initially supported by surface tension, but collapses at the point of maximum zonal separation. When a fibrin clot is entrained within the rejoined parts, it will align in a direction parallel to the direction of the relative motion between the zones. In this manner, a thread appears between the parts as they are being separated. This thread is indicative of a clot, wherein the which clot is capable of being detected by visual or electrical means.

U.S. Pat. No. 3,486,859 entitled BLOOD ANALYZING METHOD AND APPARATUS issued on Dec. 30, 1969 to R. Greiner et al. This patent depicts a blood analyzing method and apparatus including a double arm holder having blood liquid reactant chambers which communicate with each other via a small capillary conduit. An air pump is provided for applying pressure changes to one of the chambers to effect periodic mixing of the liquids via the capillary conduit. An indicator means is included to detect the progressive restriction of the capillary conduit upon coagulation of the blood.

U.S. Pat. No. 3,695,842 entitled METHOD AND SYSTEM FOR ANALYZING A LIQUID issued on Oct. 3, 1972 to M. D. Mintz, and assigned to the assignee herein. The patent describes in detail a magnetically coupled mechanical blood clot detection system wherein a variable conductance device is disposed adjacent to a zone containing a liquid and a member. A predetermined variance in the conductance of the device is detected upon change in magnetic flux lines when the liquid transforms itself and the member is displaced. The signal is produced at the time the predetermined variation in conductance has been detected.

An improved system means for measuring clotting time is disclosed in U.S. Pat. No. 3,836,333 entitled "SYSTEM FOR TIMING THE COAGULATION OF BLOOD" issued to Michael D. Mintz, on Oct. 30, 1972 and assigned to International Technidyne corporation, the assignee herein. An electromagnetic bias coil, which is wound around the reed switch, provides steady-state magnetic flux lines that supplement the flux lines provided by the permanent magnet. When the density of the flux lines passing through the reed switch decreases, as a result of the magnet being displaced, the reed switch opens. The bias coil also provides a magnetic pulse, which forces the reed switch to a closed state. This system is manufactured under the trademark HEMOCHRON® by International Technidyne Corporation at Edison, N.J.

U.S. Pat. No. 3,890,098 entitled MACHINE FOR THE DETERMINATION OF PROTHROMBIN TIME AND P.T.T. issued on Jun. 17, 1975 to E. Moreno. This patent describes a reactive material which is placed in a cup which communicates with a second cup via a restricted orifice. Plasma is placed in the second cup and the reactive material and plasma are moved from cup to cup by a pump until coagulation of the plasma takes place. Means are then provided for stopping the motion of the mixed reactive material and plasma. Other means are provided for measuring the time required for coagulation.

U.S. Pat. No. 3,951,606 entitled APPARATUS FOR PROTHROMBIN TESTING issued on Apr. 20, 1976 to R. Moyer et al. This patent shows a manually operable disposable device which can measure coagulation rates. The device is a tube of a uniform bore which can accommodate a sample and contains appropriate amounts of lyophilized reagents required to conduct individual tests such as that for prothrombin time. Calibration marks on the tube are correlated in terms of these times and the position in which a liquid sample becomes immobilized as it descends down the tube corresponds to the test time. The rate of descent of the liquid is controlled by a limiting orifice or constriction or by inclining the tube to the vertical axis.

U.S. Pat. No. 4,197,734 entitled APPARATUS FOR DETERMINING BLOOD CLOTTING TIME issued on Apr. 15, 1980 to A. Rosenberg. This patent describes an apparatus which is capable of determining the clotting time of blood. The apparatus includes a support frame which supports a syringe containing a blood sample and turntable adapted to rotate at a normal rate of speed. Blood from the syringe drops onto the turntable where the clotting time is automatically and graphically depicted by a chart rotatively carried upon the turntable. The apparatus can also be employed to determine variations in the viscosity of blood plasma and other fluids.

U.S. Pat. No. 4,725,554 entitled METHOD FOR MEASURING BLOOD COAGULATION TIME issued on Feb. 16, 1988 to K. Schildkenecht. This patent shows a method for measuring the coagulation time of a blood sample, in which a sample reagent mixture is formed by introducing the sample and at least one reagent into a cuvette. The sample reagent mixture is moved in a stationary cuvette so that the mixture flows back and forth around an edge projecting in to the cuvette whereby a clot forms and is detected on this edge.

U.S. Pat. No. 4,659,550 entitle METHOD AND APPARATUS FOR MEASURING BLOOD COAGULATION TIME is the parent of U.S. Pat. No. 4,725,554 and essentially describes the same system further utilizing photocell detectors to determine a clot formation.

From the above-cited patents, it can be seen that many devices have been made that are capable of performing a coagulation time test. However, most of these prior art devices are designed for use in a medical laboratory environment. Few of these devices are portable and simple enough to operate by a patient in his or her home. Furthermore, the prior art devices only provide the user with a single test result for the current blood sample. None of the cited references are capable of analyzing the current blood sample in view of previously stored results in order to provide a historical analysis and a means to have statistical process control over the long time use of warfarin.

One of the most difficult aspects of using the cited prior art test devices is the taking of the blood sample from the patient and the administration of the blood sample to the testing equipment. In many cases, the taking of blood requires a syringe or evacuated tube and the administration of the blood to the test equipment requires complex measurements and the use of pipettes. Obviously, such devices are not intended for unassisted home use.

A need therefore exits in the art for a portable, reliable and accurate self contained blood coagulation testing device that is simple to use and can be used at home by an unassisted patient.

A need also exists in the art for a blood coagulation testing device that has a simple means for donating the blood sample from the patient and properly administering the blood sample to the testing device.

A further need exists for a personal blood coagulation testing device that stores multiple readings from a single patient over a given period of time and presents a historical analysis of a current test.

These needs are provided for by the present invention as described and claimed below.

SUMMARY OF THE INVENTION

The present invention is a self contained, portable device for performing blood coagulation tests on a patient's blood. Blood is first drawn from a patient using a lancet. The blood is then supplied to a disposable cuvette placed within the testing device. The blood is drawn into multiple conduits within the cuvette. In a preferred embodiment, each of the conduits contain a dried prothrombin time reagent that is rehydrated by the blood. The blood in each of the conduits is then reciprocally moved across a restricted region until a predetermined degree of coagulation occurs. Since the coagulation time is being monitored in multiple conduits, a median coagulation time for a given sample can be determined.

In at least one of the conduits a normalizing control agent is present. The normalizing control agent counteracts any effects of warfarin present in the blood sample, thereby allowing the blood sample to have generally normal coagulation characteristics. The normalized blood is tested simultaneously with the untreated blood to provide a quality control reference value against which the quality of the reagents and the functionality of the system can be judged. The normalizing control agent is capable of normalizing the effects of warfarin in a blood sample across a large range of clotting factor differences. The normalizing control agent includes Vitamin K clotting factor concentration purified from normal plasma, barium citrate eluate, gluconic acid, buffers and stabilizers.

Another reference value is obtained by placing an anticoagulant in one of the cuvette conduits to produce an abnormal control agent. The abnormal control agent is also tested simultaneously with the untreated blood to provide a second quality control reference value against which the upper range of coagulation times can be judged.

BRIEF DESCRIPTION OF THE DRAWINGS

For a better understanding of the present invention, reference is made to the following description of exemplary embodiments thereof, considered in conjunction with the accompanying drawings, in which:

FIGS. 6a–6i show the cycle of the flow of blood in the cuvette past the electrooptical sensors;

DETAILED DESCRIPTION OF THE INVENTION

Figure 1:
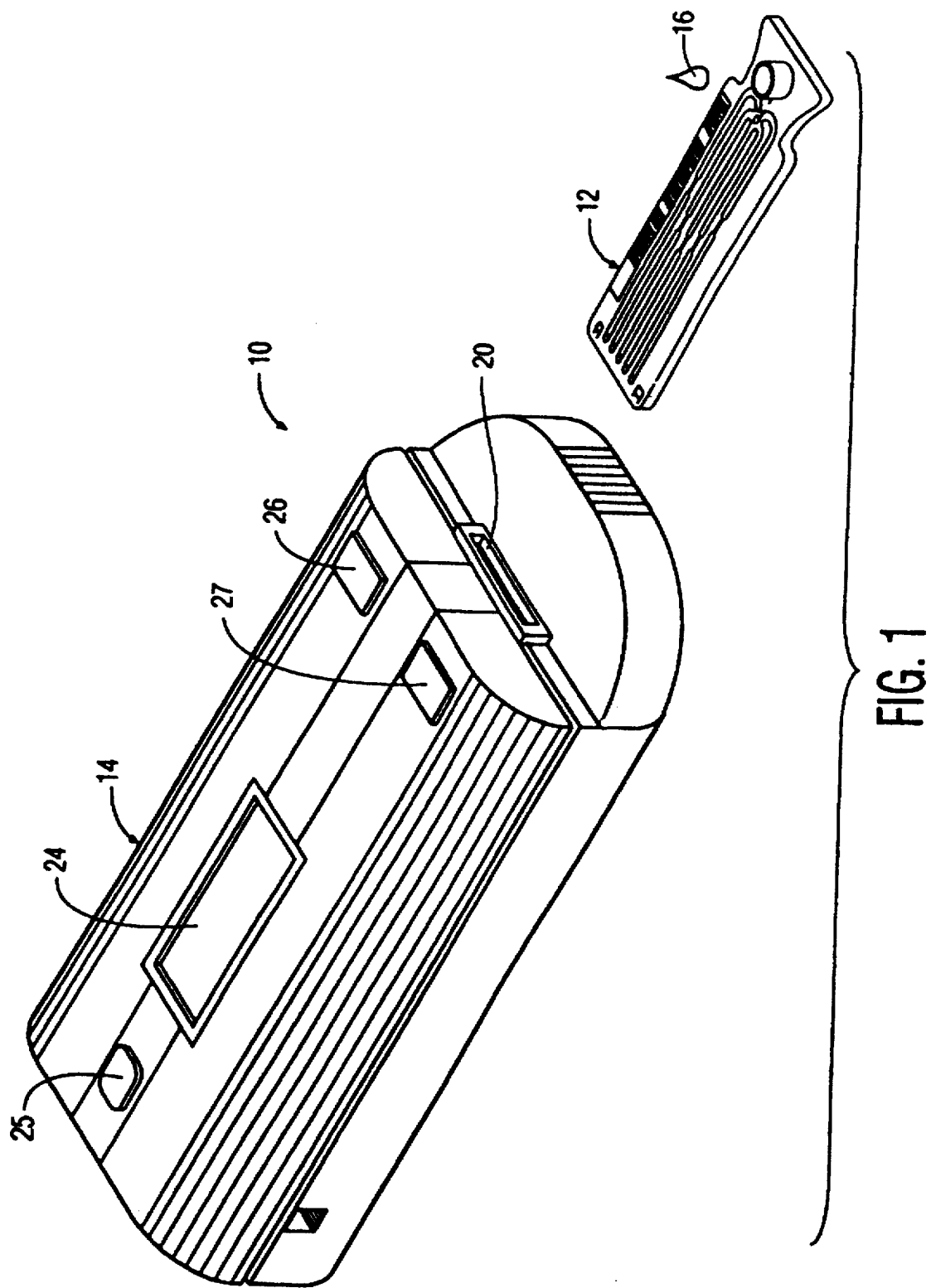
FIG. 1 is a perspective view of one preferred embodiment of the present invention cuvette and blood coagulation testing apparatus.

The present invention is an apparatus and method for determining the coagulation time for the blood of a patient, especially a patient who is taking an anticoagulation drug such as warfarin. Referring to FIG. 1, there is shown one preferred embodiment of the present invention apparatus 10. The apparatus 10 is a self-contained portable testing instrument designed to provide a simple, user friendly blood coagulation analysis, i.e. prothrombin time (PT) test, to either the user or the user's physician. In the shown embodiment, the apparatus 10 consists of a disposable cuvette 12 and the actual testing device 14. To utilize the present invention apparatus 10, a sample of blood 16 is placed within the cuvette 12. The disposable cuvette 12 is inserted into the testing device 14 through slot 20. The testing device 14 tests the blood sample 16 within the disposable cuvette 12 without contacting the blood sample 16. Accordingly, once the PT test has been completed, the cuvette 12 can be removed from the testing device 14 and disposed. Another cuvette can then be entered into the testing device 14 without the need to sterilize or otherwise clean the testing device 14.

A display 24 is disposed on the top of the testing device 14. As will be later be explained, the display 24 can display either the results of a test just preformed, or may display a historical analysis of previously stored test results. Various control buttons 25, 26, 27 are also disposed on the testing device 14 for the purpose of starting the device, controlling the display and accessing stored data from memory.

Figure 2:
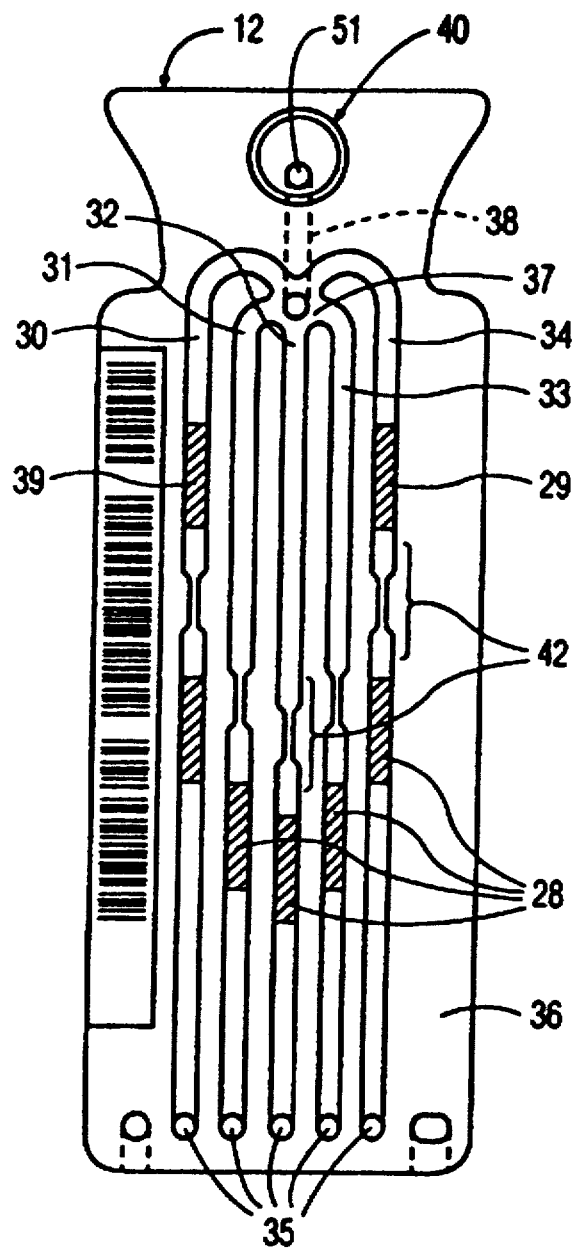
FIG. 2 is a top view of one preferred embodiment of the present invention cuvette.

Referring to FIG. 2 there is shown a top view of one preferred embodiment of the disposable cuvette 12. The cuvette 12 has a substantially planar structure made from a transparent material. Within the cuvette 12 are five channels or conduits 30, 31, 32, 33, 34. The number five is preferred, however fewer or greater numbers of conduits could be used. The distal ends of each of the five conduits 30, 31, 32, 33, 34 terminate at drive apertures 35 that extend through the upper surface 36 of the cuvette 12. The ends of each of the conduits 30, 31, 32, 33, 34 opposite the drive apertures 35 each terminate a common supply area 37 contained within the cuvette 12. Blood is supplied to the common supply area 37 by a supply conduit 38 that selectively couples to a supply reservoir 40 in a manner that will be later explained. Each of the conduits 30, 31, 32, 33, 34 within the cuvette 12 contains a restricted area 42 where the internal area of the conduit rapidly narrows. The internal surface of the restricted areas 42 inside each of the conduits 30, 31, 32, 33, 34 is preferably roughened or otherwise textured to promote the coagulation of blood in the restricted areas 42 as blood travels through the various conduits 30, 31, 32, 33, 34.

A clot promoting reagent 28 is disposed in each of the conduits 30, 31, 32, 33, 34 within the cuvette 12 in between the restricted areas 42 and the drive apertures 35. The clot promoting reagent 28 is a prothrombin time reagent such as dried rabbit brain thromboplastin at approximately 30 mg/ml, however other clot promoting reagents can be used, such as tissue factor. The dried control agent 28 is placed within each of the conduits 30, 31, 32, 33, 34 wherein presence of blood in the conduits rehydrates the clot promoting reagent 28, thereby mixing the clot promoting reagent 28 with the blood. The thromboplastin reagent is preferably dried by a water extraction technique such as lyophilization within the conduits 30, 31, 32, 33, 34. The middle three conduits 31, 32, 33 are the sample test conduits that will be used for the actual blood sample analysis. The first conduit 30 is an abnormal control channel and the last conduit 34 is a normal control channel. In the middle three conduits 31, 32, 33 the blood sample tested and the results are averaged to ascertain the actual analytical value of the sample. As will be explained, in the normal control channel 34 the blood sample is normalized prior to reaching the restricted area by the blood passing through an appropriate normal control agent 29. The normalized blood is then tested to provide the testing device with a normal blood sample for reference.

The normal control agent 29 preferably consists of an air dried mixture, containing at least one Vitamin K dependent clotting factor concentrates, barium citrate eluate, barbital buffered saline, trehalose, malto dextrin and thimerosal. The Vitamin K dependent clotting factors concentrates are obtained through a fractionation technique, employing column chromatography which may be preformed in conjunction with selected protein absorbs (i.e. barium citrate). Such techniques are known in clinical hematology. The Vitamin K dependent factor concentrates are prepared from human pooled plasma with or without bovine pooled plasma. Several manipulations in the manufacture of the normal control agent 29 result in a stable preparation. These manipulations includes adding the two Vitamin K dependent factor concentrates and barium citrate eluate separately to a plasma with a different degree to find out the concentrations of the two coagulation factor concentrates that will bring the abnormal plasma to a normal or close to normal prothrombin time. The two coagulation factor concentrates are then mixed and buffered, and both stabilizers and thimerosal are added. The concentration is then adjusted and the reagent is air dried and packaged.

The normal control agent 29 may also contain gluconic acid, calcium salts and heparin to decrease or increase coagulation clotting time. However, the preferred normal control agent 29 composition is as follows:

|  | Vitamin K Dependent Clotting Factor | Eluate | GAC | Trehalose | M700 | BBS |
|---|---|---|---|---|---|---|
| Min | 1.0 u/ml | .009 u/ml | .008 M | 3.0% | 2% | buffer |
| Max | 3.5 u/ml | .035 u/ml | .03 M | 8.0% | 6% | buffer |

One example of a Vitamin K dependent clotting factor concentrate is a Factor IX complex (Konyne 80), purchased from Miles Inc. The Eluate is barium citrate eluate, purchased from Sigma Chemical Company. The GAC is gluconic acid with calcium salts, purchased from Sigma Chemical Company. The Trehalose is purchased from Sigma Chemical Company. The M700 is Malto dextrin, purchased from Grain Processing Corporation. Finally, the BBS is Barbital, sodium salt, purchased from Sigma Chemical Company.

In the first conduit 30, within the cuvette 12, an abnormal control agent 39 is disposed between the restricted area 42 and the common supply area 37. The abnormal control agent 39 is rehydrated by the blood in the first conduit 30, wherein the abnormal control agent 39 mixes with the blood and provides the blood with known abnormal clotting characteristics. The composition of the abnormal control agent 39 is preferably the same as the composition of the normal control agent previously listed with the addition of between 0.5 u/ml and 3.0 u/ml of heparin, with or without the elimination of the GAC. As will be explained, the blood in the first conduit 30 that mixes with the abnormal control agent 39 is tested simultaneously with the blood in the middle three conduits 31, 32, 33 and the normalized blood in the last conduit 34. The testing of the abnormal sample assures the quality and integrity of the blood sample used in determining the test results of the middle three conduits 31, 32, 33. The use of a normal sample, an abnormal sample and multiple test samples enables the clotting time performance of the sample blood to be accurately evaluated irrespective of the clotting characteristics of the blood sample being tested. Accordingly, the effect of the anticoagulation drug in the blood can be accurately measured despite the effects of other drugs or the coagulation characteristics of the patient's blood prior to the administration of the anticoagulant. Testing the normalized blood in conduit 34 and the abnormal blood in conduit 30, assures that the blood sample collection, the test reagents employed in the cuvette and the testing instrument are all within the preestablished performance specifications. This level of internal quality control assures the health care provider (i.e. patient physician) that the prothrombin time test results accurately reflect the level of patient's blood coagulation.

Figure 3A:
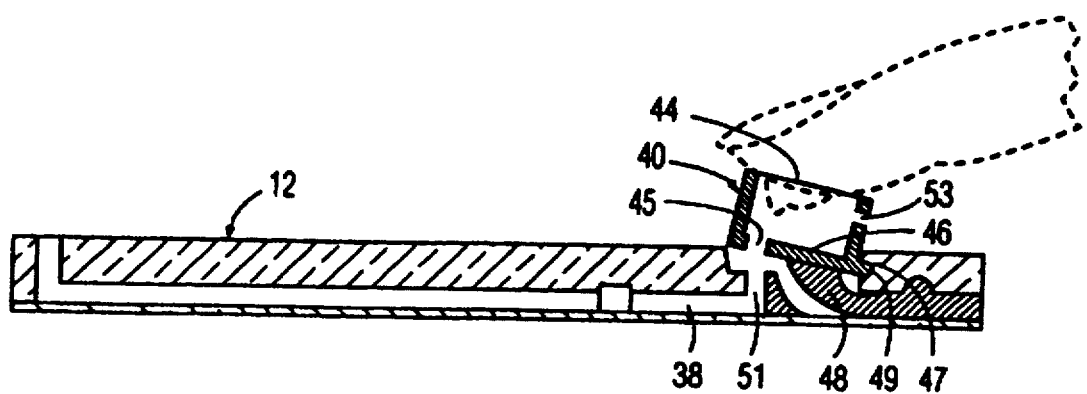
FIG. 3a is a cross-sectional view of the embodiment of the cuvette shown in FIG. 2, viewed along section line 3—3.
Figure 3B:
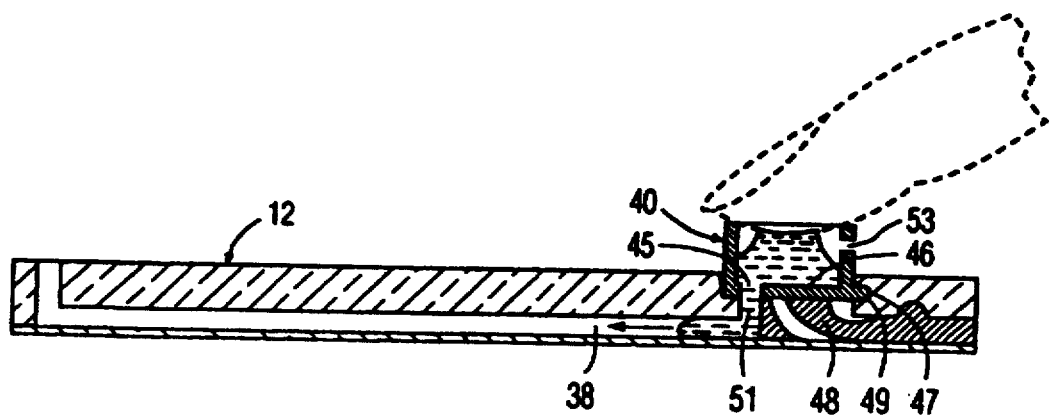
FIG. 3b is a cross-sectional view of the embodiment of the cuvette shown in FIG. 2, viewed along section line 3—3, and shown in conjunction with a lanced finger supplying blood to the cuvette.

Referring to FIG. 3a in conjunction with FIG. 2 it can be seen that supply reservoir 40 on the cuvette 12 is a cup-like structure having an open top 44 and a small aperture 45 on its bottom surface 46. In the shown embodiment, the supply reservoir 40 is supported at an angle relative to the horizontal by a flexible pawl 48. The supply reservoir 40 also is coupled to the cuvette 12 by a small protrusion 49 that enters a recess 47 disposed within the material of the cuvette 12. Below the supply reservoir 40 is an opening 51 that leads to the supply conduit 38. Referring to FIG. 3a in conjunction with FIG. 3b it can be seen that a blood sample is administrated to the supply reservoir 40 by a person pricking his/her finger and placing the pricked finger over the supply reservoir 40. The weight of the finger on the supply reservoir 40 causes the flexible pawl 48 to yield. This causes the supply reservoir 40 to pivotably rotate into a horizontal position as guided by the pivot that is created by the presence of the protrusion 49 in the recess 47. As the supply reservoir 40 rotates into the horizontal, the aperture 45 on the bottom surface 46 of the supply reservoir 40 aligns and abuts against the opening 51 that leads to the supply conduit 38. Once aligned and in abutment, low pneumatic pressure in the supply conduit 38 draws blood out of the supply reservoir 40 and into the supply conduit 38. During such a transition, the person's finger is covering the open top 44 of the supply reservoir 40. In order to prevent a vacuum from forming in the supply conduit 38, a vent aperture 53 is formed in the wall of the supply reservoir 40, below the finger. This allows air to flow into the supply reservoir 40, thereby preventing any back pressure from restricting the flow of blood out of the supply reservoir 40. As will later be explained, the placement of a finger on the cuvette is only one way of filling the cuvette with a blood sample. In alternate embodiments blood can be transferred to the cuvette in a sample cup or a customized lancet, both of which will be later described.

Figure 4A:
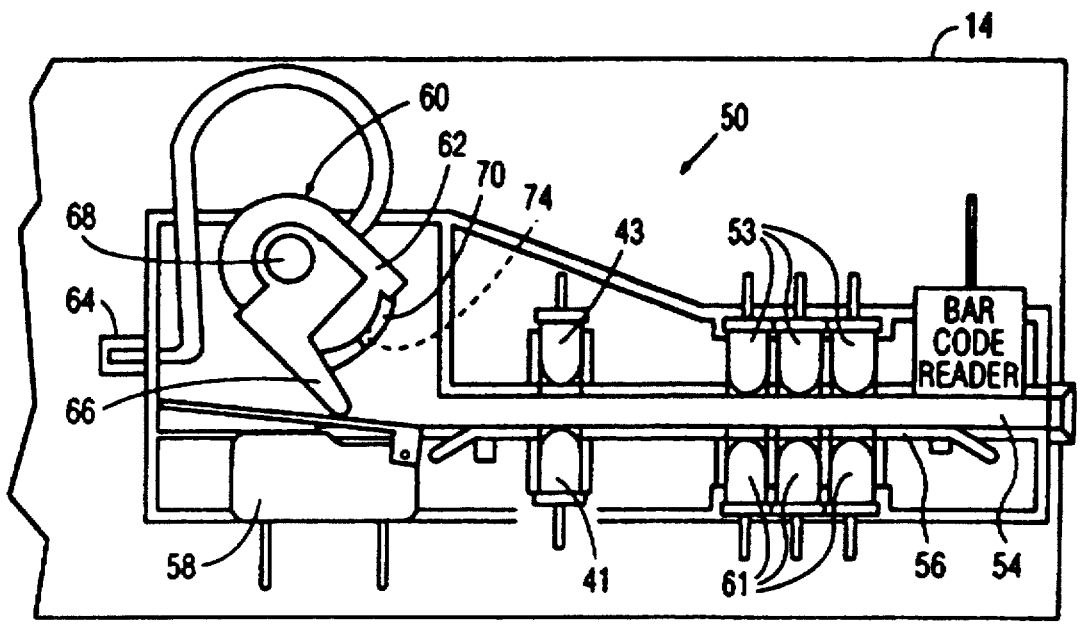
FIG. 4a is a cross-sectional view of a segment of the blood coagulation time testing apparatus shown in FIG. 1.
Figure 4B:
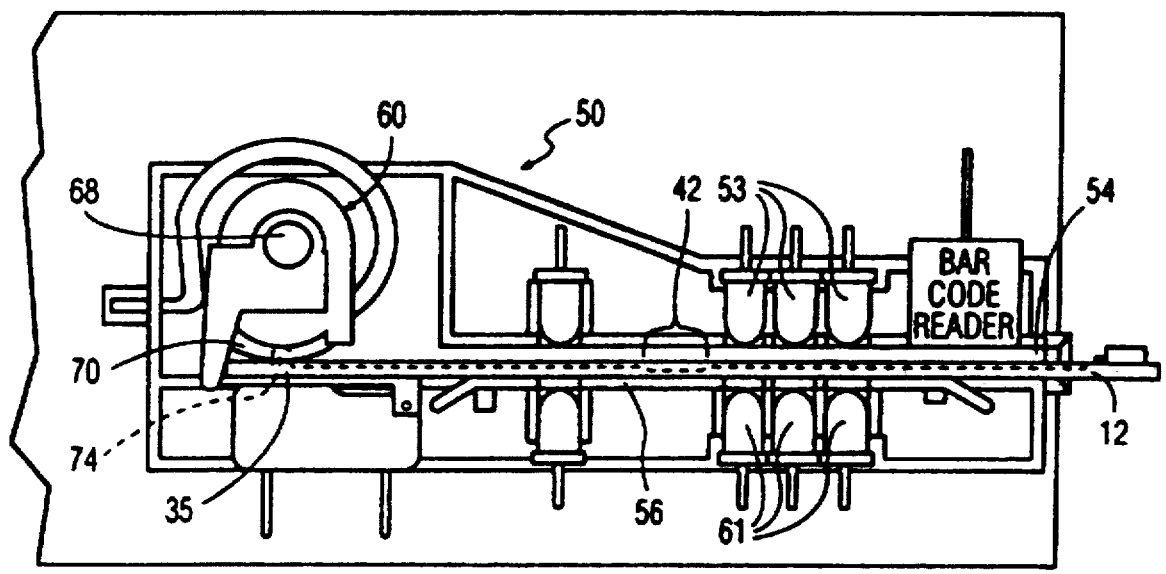
FIG. 4b is the same cross-sectional view as is shown in FIG. 4a with the addition of having a cuvette inserted into the blood coagulation time testing apparatus.

To use the present invention, a clean cuvette 12 is placed with the test device 14 (FIG. 1). Referring to FIG. 4a it can be seen that a testing interface unit 50 is disposed within the testing device 14. The cuvette enters the test device 14 via the slot 20. The slot 20 leads into a channel 54 shaped to receive the cuvette within the testing interface unit 50. Below the channel 54 is positioned a heating element 56 such as a foil heater or the like which is used to heat the cuvette when it is within the channel 54. At the distal end of the channel 54, opposite the entrance slot 20, are positioned a proximity switch 58 and a pneumatic manifold assembly 60. The pneumatic manifold assembly 60 consists of five manifold members 62 of which only one is shown in FIGS. 4a and 4b. Each manifold member 62 is pneumatically coupled to a tube 64. The tubes 64 lead to pneumatic sources (not shown) capable of periodically supplying both positive and negative pressures relevant to the ambient pressure. A rocker arm member 66 extends downwardly from each the manifold members 62. Each manifold member 62 has an orifice formed through its structure through which an axle rod 68 may pass. Consequently, the whole pneumatic assembly 60 is pivotably rotatable around axle rod 68. At the base of each manifold member 62 is positioned an elastomeric seal 70 having a central orifice 74. The central orifice 74 pneumatically communicates with the manifold member 62 and the respective tubes 64 that lead to the pneumatic sources.

Proximate the center of the channel 54 are positioned a plurality of photoelectric sensors 61 positioned on one side of the channel 54 directly across from light sources 53 which may be incandescent bulbs, light emitting diodes or the like. In the preferred embodiment three photoelectric sensors 61 are used, however additional photoelectric sensors may be added. As will be later explained, the photoelectric sensors 61 and light sources 53 are positioned within the testing interface unit 50 at positions that correspond to the five conduits 30, 31, 32, 33, 34, 35 (FIG. 2) in the cuvette 12 when the cuvette 12 is placed within the testing interface unit 50. As such, light emissions from the light sources 53 to the photoelectric sensors 61 must pass through to a material of the cuvette 12, the conduits 30, 31, 32, 33, 34 and the material contained within the conduits 30, 31, 32, 33, 34. A forth photoelectric sensor 41 and source 43 are disposed at the far end of the channel 54. The fourth photoelectric sensor 41 and light source 43 serve as a fail safe detector that prevents blood from being drawn into the manifold member 62.

In FIG. 4b the testing interface unit 50 of FIG. 4a is depicted in combination with the cuvette 12. As can be seen, when the cuvette 12 is inserted into the channel 54, the cuvette 12 rotates the pneumatic manifold assembly 60 around the axle 68. Consequently, the elastomeric seals 70 on each of the manifold members 62 rotate against the material of the cuvette 12. As the elastomeric seals 70 rotate and contact the cuvette 12, the orifice 74 on the elastomeric seal 70 aligns with the drive aperture 35 of the corresponding conduit in the cuvette 12. The contact between the elastomeric seals and the cuvette 12 create an air tight seal, as such each of the manifold members 62 becomes pneumatically coupled to a corresponding conduit 30, 31, 32, 33, 34 within the cuvette 12.

The placement of the cuvette 12 fully within the testing interface unit 50 positions the restricted areas 42 and surrounding regions of the five conduits above the heating element 56. Consequently, blood contained within the cuvette 12 can be raised to, and maintained at, a predetermined temperature for testing, despite variations in the surrounding ambient temperature or the original temperature of the cuvette 12. The placement of the cuvette 12 within the testing interface unit 50 also positions the restricted areas 42 of the five conduits 30, 31, 32, 33, 34, proximate five corresponding sets of photoelectric sensors 61. Consequently, the presence of blood in any one of the conduits 30, 31, 32, 33, 34, can be detected on the supply side of the restricted areas 42 in each of the conduits by the photoelectric sensors 61. Furthermore, the placement of the cuvette 12 fully into the testing interface unit 50 causes a bar code or other indicia to be read by a scanner. This identifies the curvette and notifies a central control unit that a cuvette 12 has been entered into the test device 14 for testing.

Figure 5:
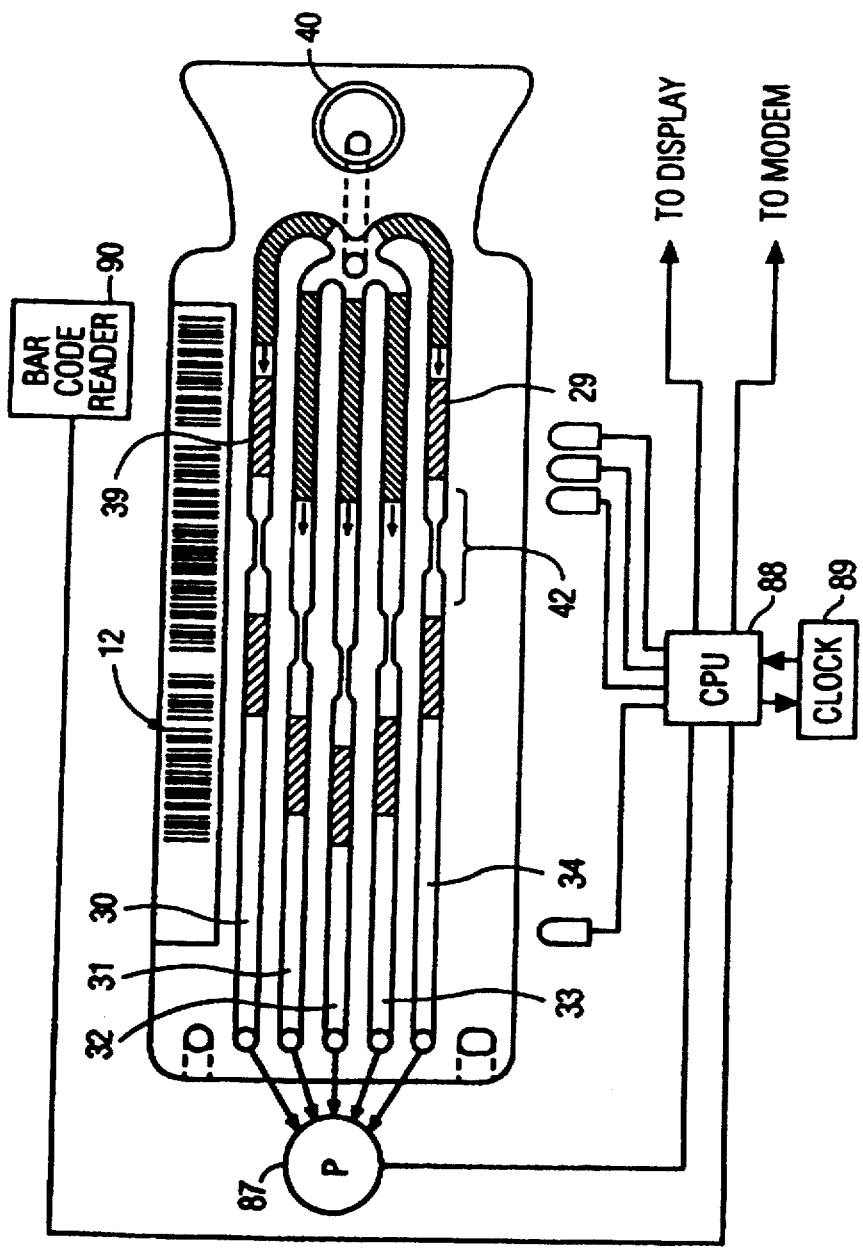
FIG. 5 shows a top view of the present invention cuvette shortly after blood is drawn into each of the five conduits contained within the cuvette.

Referring now to FIG. 5 in conjunction with FIG. 4b, the operation of the present invention can be described. To begin a blood coagulation time test on a sample of blood, the cuvette 12 is inserted into the test device 14. Once in place, the supply reservoir 40 is filled with a sample of blood in a manner which will be later explained. Once inserted in to the test device 14, the five conduits 30, 31, 32, 33, 34 become pneumatically coupled to the manifold assembly 60 and a pneumatic source 87 coupled to the manifold assembly 60 by the tubes 64 (FIG. 4b), in the manner previously described. In FIG. 5, a newly inserted cuvette 12 is shown where the sample of blood is newly drawn from the sample reservoir 40, by pneumatic pressures that are applied to the five conduits 30, 31, 32, 33, 34. As such, the blood is drawn out of the sample reservoir 40, through the supply conduit 38 and an equal amount is drawn into each of the five conduits 30, 31, 32, 33, 34.

The sample reservoir 40 is capable of retaining at least one hundred micro liters of blood from the patient's fingertip. Once the cuvette 12 is properly placed in the testing device, the pneumatic source 87 reduce the pressure within the five conduits 30, 31, 32, 33, 34. The low pressure is maintained until ten microliters of blood are drawn into each of the five conduits 30, 31, 32, 33, 34. As the blood in the normal control conduit 34 and the abnormal control conduit 30 are drawn toward the restricted areas 42 in each conduit, the blood rehydrates the normal control agent 29 and the abnormal control agent 39, respectively, present within those conduits. In these two conduits, the blood sample is therefore altered prior to the blood sample traversing the restricted areas 42. As the blood sample travels through each of the conduits 30, 31, 32, 33, 34 passes across the optical array of the three photoelectric sensors 61. As the blood sample crosses the photoelectric sensors 61 for the first time the sensors 61 can be used to measure sample size and sample position relative to one another and relative to the expected position as determined from the pneumatic source 87.

The pneumatic source cycles back and forth causing the blood sample in each of the conduits 30, 31, 32, 33, 34 to reciprocally flow pass the restricted region 42. As the blood sample in each of the conduits 30, 31, 32, 33, 34 begins to coagulate, fibrin forms and occludes the restricted regions 42 within the conduits 30, 31, 32, 33, 34. The occlusions eventually stop or substantially slow the flow of blood. In the process of pumping the blood sample past the restricted region 42, the process of fibrin formation can be disrupted by the velocity change of the blood as it enters the smaller diameter restricted region 42. This disruption is especially significant in highly anticoagulated specimens. In order to compensate for the velocity change the cycled flow of the blood sample is decreased over time in order to allow additional time for clots to form in the unrestricted portions of the blood sample. The decrease is implemented on a time weighted basis such that the system resolution can be optimized to a percentage of total elapsed time. For example, continuously decreasing the rate of oscillation by 5% enables one to resolve fast forming clots within fractions of a second and resolve slow forming clots of highly anticoagulated samples well within the overall test time.

Referring to FIGS. 6a–6i, the actual testing cycle is illustrated. The blood sample is drawn past the three photoelectric sensors 61 into the restricted region in each of the conduits present within the cuvette. Once drawn through the restricted region the blood sample rehydrates and mixes with the clot promoting reagent 28 (FIG. 2) present within each of the conduits. In FIG. 6a the blood sample is shown within the restricted region 42 but not obstructing any of the three photoelectric sensors 61. As such, the three photoelectric sensors 61 produce a (0,0,0) signal as indicated in FIG. 6a. When the blood sample is clear of the three photoelectric sensors 61 and is within the restricted region 42, a counting cycle is begun on an internal clock 89 (FIG. 5). The pneumatic source 87 reverses and pushes the blood sample through the restricted region and back toward the three photoelectric sensors 61. As can be seen in FIGS. 6b, 6c and 6d, the first photoelectric sensor becomes obscured as does the second and third photoelectric sensor in turn. As a result, the signal received from the photoelectric sensors 61 changes from (0,0,0) to (1,1,0) to (1,1,0) and finally (1,1,1) once all the photoelectric sensors 61 are obscured. Once the (1,1,1) signal is received by the C.P.U. 88 (FIG. 5) the pneumatic source 87 is reversed and the blood is drawn back through the restricted region 42. In FIGS. 6e, 6f, 6g and 6h it can be seen that once the pneumatic source 87 is reversed the signal received from the photoelectric sensors 61 change from (1,1,1) to (1,1,0) to (1,0,0) and finally back to (0,0,0). Once the (0,0,0) signal is received by the CPU 88 (FIG. 5), the pneumatic source 87 is again reversed and the cycle is repeated.

Returning to FIG. 5, it will be understood that as the cycles of movement repeat the blood sample begins to coagulate in the restricted areas 42 of the five conduits 30, 31, 32, 33, 34. The coagulation is promoted by the roughened surfaces each of restricted areas 42. As such, with each cycle the occlusion presented by the restricted areas 42 increases. Consequently, one coagulation has begun, each cycle takes more time than the previous since the opening being traversed by the flowing blood sample becomes smaller. At the same time, the rate at which the column of blood is oscillated or driven back and fourth is decreased. The decrease is implemented on a time weighted basis such that the system resolution can be optimized to a percentage of total elapsed time.

For each cycle the CPU 88, via internal clock 89, counts the time for the cycle and compares it to the previously cycle time. When any one cycle time is a predetermined amount of time longer than the previous cycle time, the CPU 88 considers coagulation to have occurred and the overall time for coagulation is displayed. For example, in one preferred embodiment of the present invention, it has been determined that a substantial change between subsequent cycle times indicates coagulation has occurred. As such, if one cycle took four seconds and the next cycle took five seconds, the CPU 88 would stop the test and display the elapsed time taken for coagulation to occur. However, each of the five conduits is monitored independently. As a result, the results of the test are not displayed until coagulation has occurred in all of the conduits and the actual test results are calculating the CPU 88.

As can be seen from FIGS. 4b and 5, the cuvette 12 passes under a bar code scanner 90 when inserted into the testing device 14. A bar code 91 is disposed on each cuvette 12. The first purpose of the bar code 91 is to inform the testing device as to which type of test is being preformed, i.e. PT, APTT, etc. The bar code 91 identifies reagent standardization parameters that correspond to variations between lots such as the ISI valve for PT reagent. The bar code 91 can also prevent expired cuvettes from being tested by identifying the point of expiration for the various dried reagents contained within the cuvette. The passage of the bar code 31 under the bar code scanner 90 shows that the cuvette is properly placed within the testing machine and may also automatically start the testing sequence.

The use of a bar code and a bar code scanner is only exemplary and it will be understood that any optical or electronic identification system can be used in place of the bar code system.

In the preferred embodiment of the present invention test device, the CPU 88 is capable of retaining the results of at least ten different tests in memory for a given patient. For any one given test, the coagulation time result is compared to a predetermined maximum value and a minimum value. If the test results fall outside the acceptable range, a warning is displayed to make the patient and/or the doctor aware of the danger. The test device 14 may also include a modem jack 95 (FIG. 1) that enables the test device 14 to download information stored in memory over the telephone. A patient, using the test device 14 at home, can thereby send test data to a doctor or a hospital over the telephone.

Figure 7A:
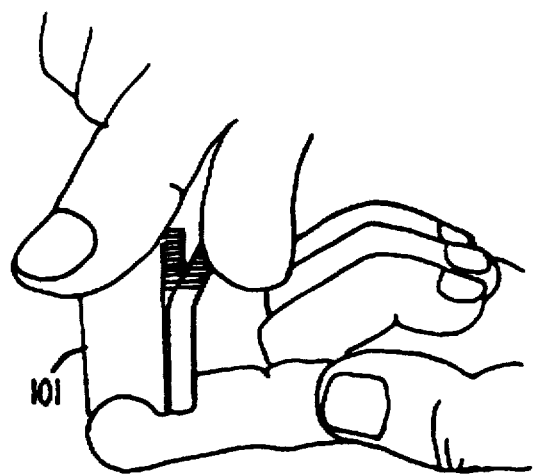
FIG. 7a shows a person using a lancet to obtain a blood sample from a finger.
Figure 7B:
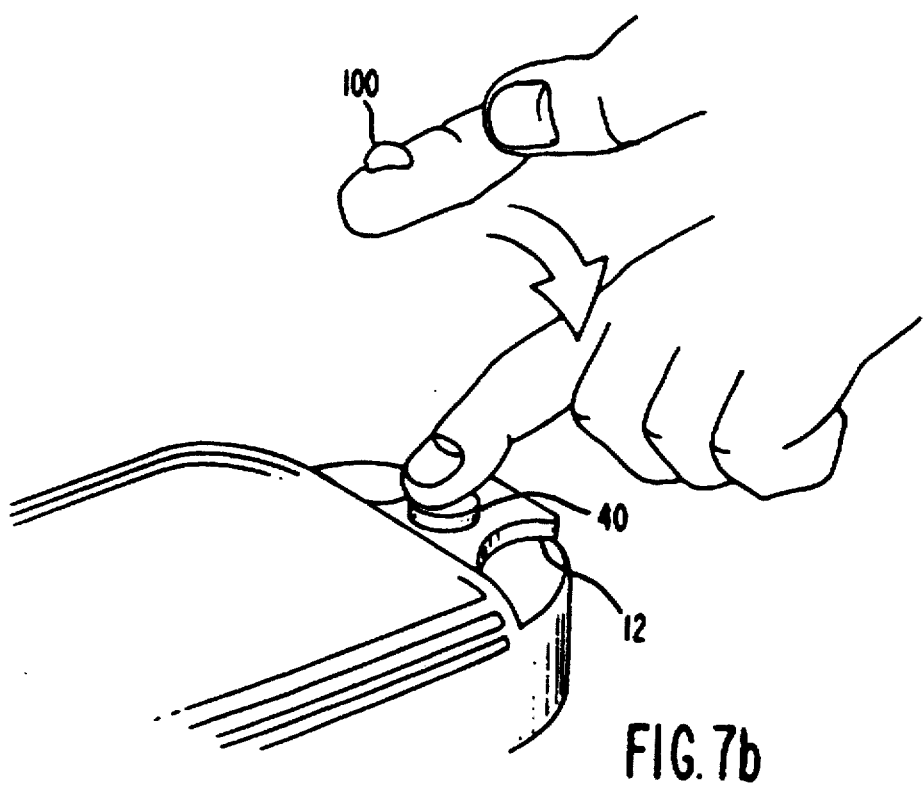
FIG. 7b shows the blood sample on the finger being supplied to the cuvette within the blood coagulation test apparatus.

In the preferred method of use, the blood sample used in testing is obtained from a finger prick. Referring to FIG. 7a it can be seen that the finger prick is preferably made by a TENDERLETT® lancet 101, as disclosed by U.S. Pat. No. 5,133,730 to Biro et al entitled DISPOSABLE-RETRACTABLE FINGER STICK DEVICE, and assigned to International Technidyne Corporation, the assignee herein, the disclosure of which is herein incorporated by reference. After the TENDERLETT® device is used to create the finger prick, the initial droplet of blood is wiped clean of the finger. An alcohol pad and gauze may be included in each test kit with the lancet to promote the proper collection technique. A second droplet of blood is then allowed to form on the finger. Referring to FIG. 7b it can be seen that the droplet of blood 100 is then directed into the sample reservoir 40 on the cuvette 12. The blood is then drawn into the cuvette 12 in the manner previously described.

Figure 8A:
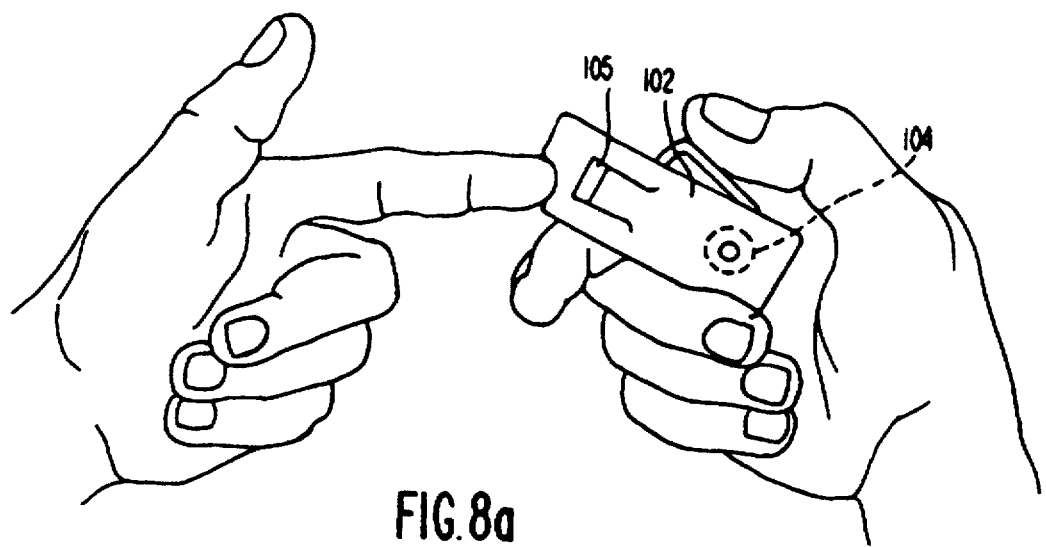
FIG. 8a shows a person using a specialized lancet to obtain a blood sample from a finger.
Figure 8B:
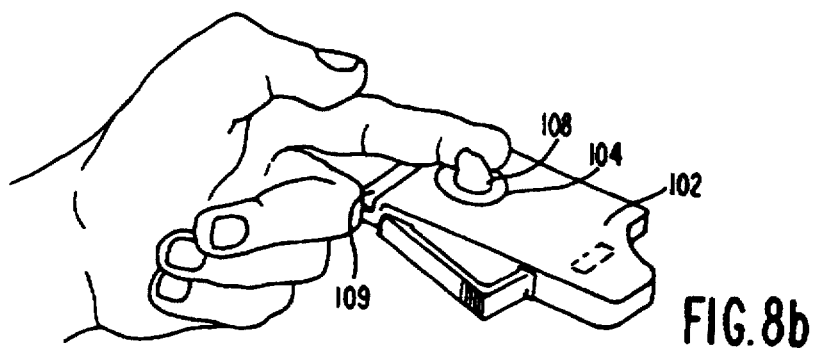
FIG. 8b shows the blood sample on the finger being supplied to a reservoir built into the lancet.
Figure 8C:
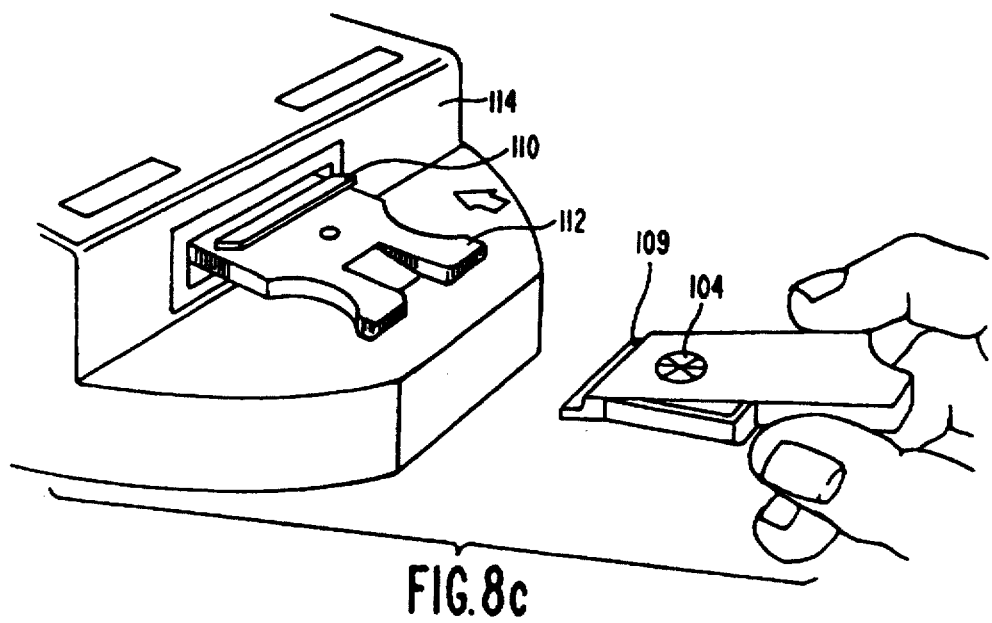
FIG. 8c shows the lancet being supplied to the blood coagulation test apparatus above the cuvette.
Figure 8D:
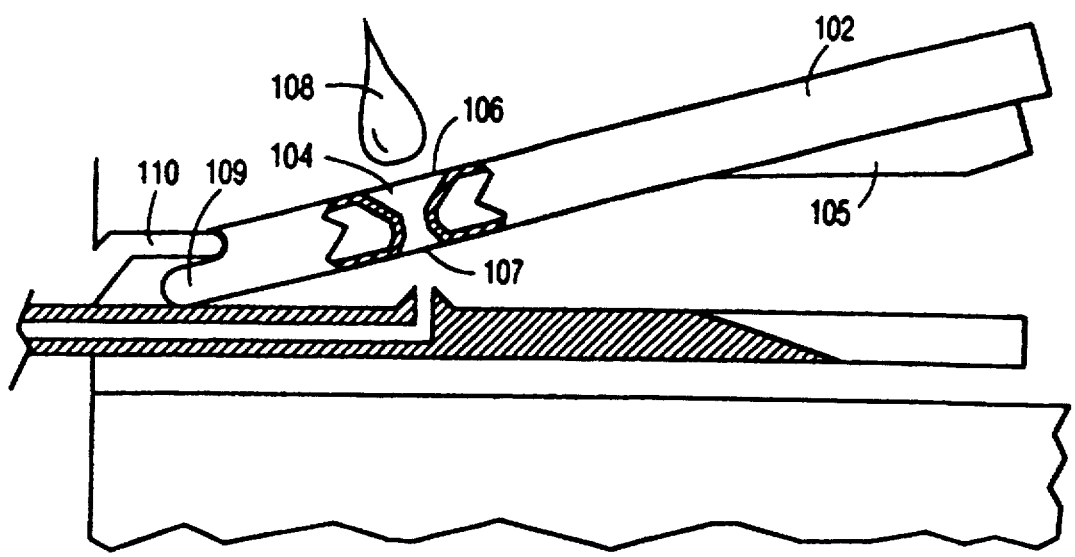
FIG. 8d shows a selective cross-sectional view of the lancet as it is applied to the test apparatus.
Figure 8E:
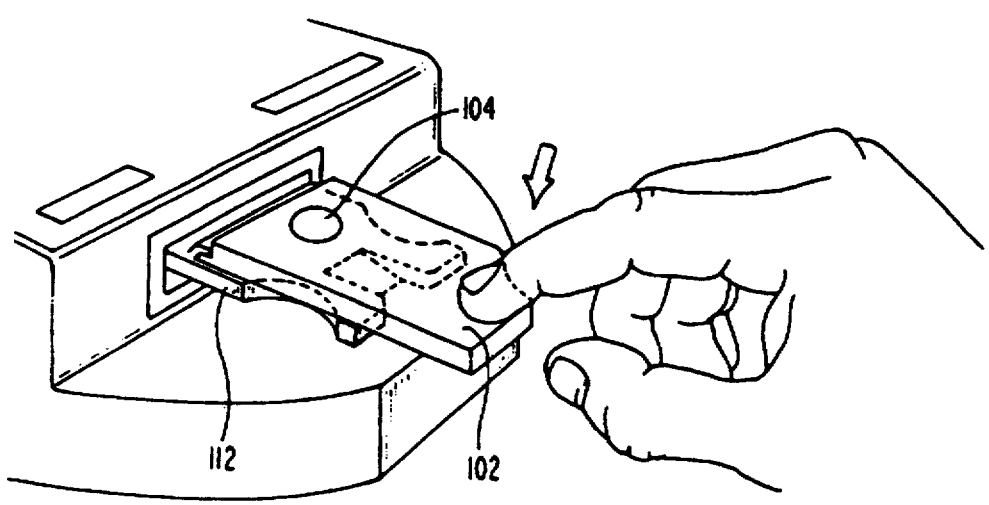
FIG. 8e shows the lancet engaging the test apparatus.

Referring to FIG. 8a the lancet 102 is used to cut a patient's finger. The lancet 102 has two modifications not currently found in a TENDERLETT® lancet. Those modifications include a funnel shaped aperture 104 that extends through the lancet 104 and a guide protrusion 105 that extends below a bottom surface of the lancet 102. Referring to FIG. 8d it can be seen that the funnel shaped aperture 104 has a large top opening 106 and a small bottom opening 107. The small bottom opening 107 is small enough so that the surface tension of blood added to the aperture 104 prevents the blood from flowing through the small bottom opening 107 unassisted. As is shown in FIGS. 8b and 8c a blood sample 108 is taken from the lanced finger and is placed in the large top opening 106 of the funnel shaped aperture 104. The lancet 102 has a ledge 109 disposed at one end that engages an overhang 110 extending from the test machine 114. Referring to FIGS. 8d and 8e it can be seen that the cuvette 112 does not have the sample reservoir as previously described, but rather has a nipple region 113 that partially passes into the aperture 104 on the lancet 102 as the lancet 102 is laid upon the cuvette 112. Once laid into place, the blood in the aperture 104 can be drawn into the cuvette 112 by a pneumatic pump as was previously described.

Figure 9A:
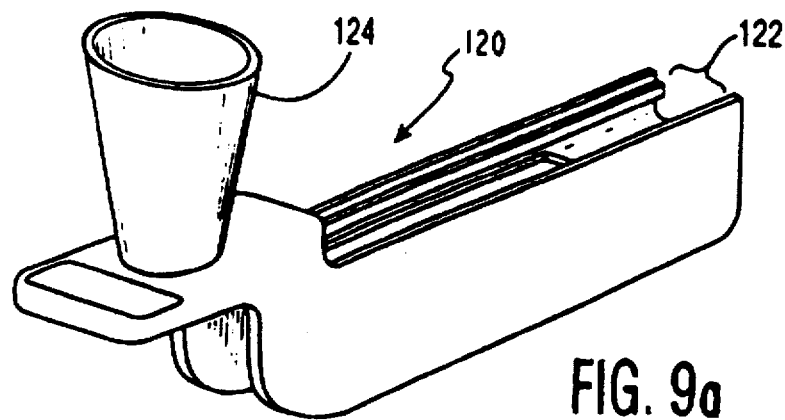
FIG. 9a shows a blood sample collection attachment that can be selectively joined to a lancet.
Figure 9B:
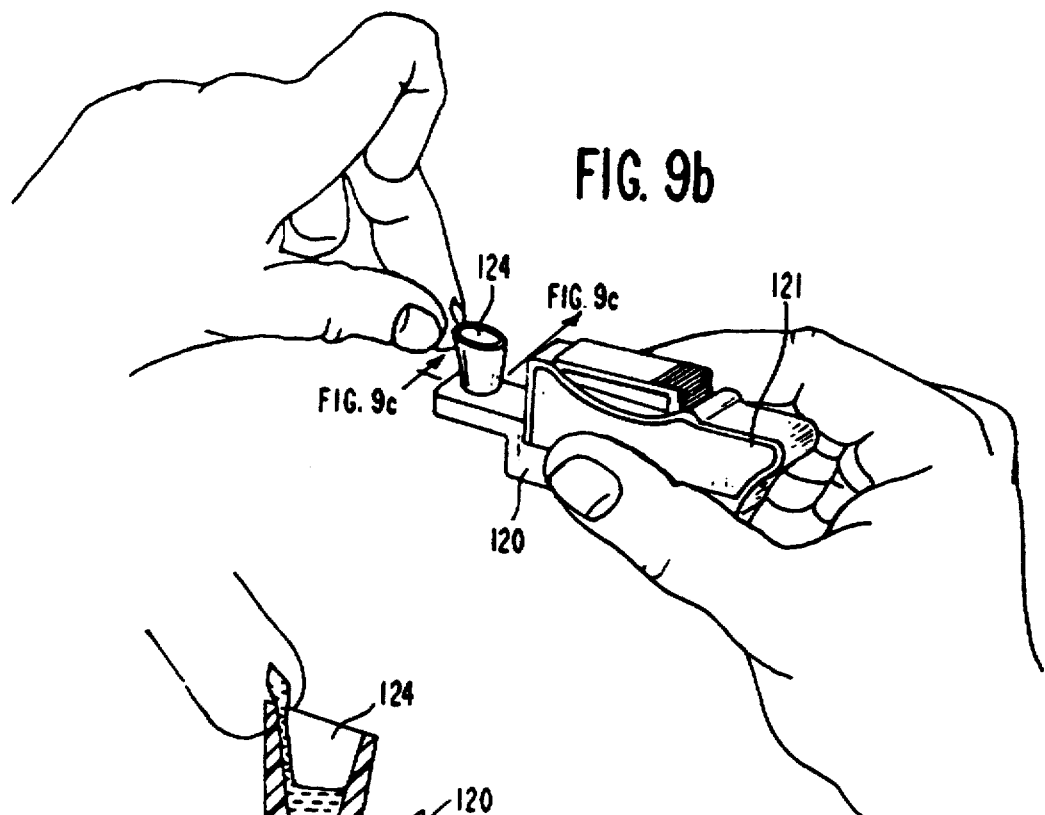
FIG. 9b shows the blood sample on a finger being supplied to the blood collection attachment when coupled to a lancet.
Figure 9C:
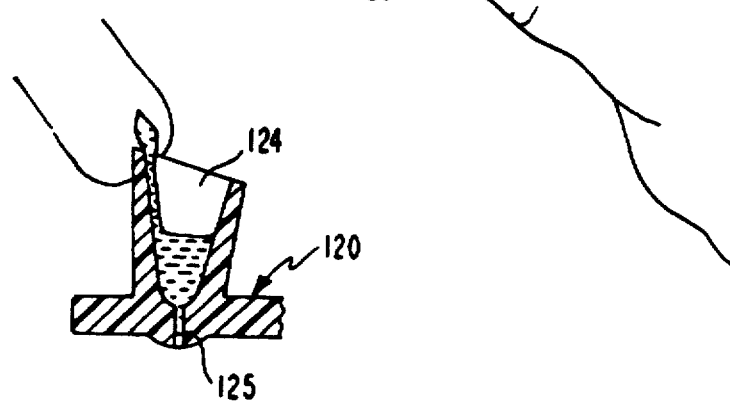
FIG. 9c shows a segment cross-sectional view of FIG. 9b, viewed along section line 9c—9c.

Referring to FIG. 9a there is shown a blood sample reservoir attachment 120 that can be attached to a TENDERLETT® lancet. The attachment 120 includes a slotted region 122 that engages the exterior housing of a TENDERLETT® lancet. A conical shaped reservoir 124 is supported by the attachment 120. The attachment 120 is preferably a disposable device that can be selectively added to a standard TENDERLETT® lancet. However, in an alternative embodiment, the attachment 120 and lancet can be integrally formed. Referring to FIGS. 9b, 9c, 9d and 9e it can be seen that the reservoir attachment 120 is added to a TENDERLETT® lancet 121, wherein the TENDERLETT® lancet is used to create a finger prick. The blood from the prick is then added to the conical shaped reservoir 124 as is shown in FIG. 9b. The entire TENDERLETT/blood sample reservoir attachment 120 is then placed into a slot 132 in the testing device 140. The conical shaped reservoir 124 aligns over an aperture in the cuvette 142, whereby blood can be drawn into the cuvette 142 from the conical shaped reservoir 124. As is shown in FIG. 9c the conical shaped reservoir 124 has a narrow channel 125 at its bottom that serves to drain the blood sample from the reservoir 124. The diameter of the narrow channel 125 is small enough so that the surface tension of the blood sample prevents the blood from draining through the narrow channel 125 unassisted. From FIGS. 9d and 9e, it can be seen that as the TENDERLETT® lancet 121 and the reservoir attachment 120 are added to the testing device 140, the conical shaped reservoir 124 aligns over an aperture 126 in the cuvette 142. The blood sample can then be drawn into the cuvette 142 from the conical shaped reservoir by creating a negative pressure in the cuvette 142.

In the embodiment of FIGS. 9a–9e, the reservoir attachment 120 is shown as a detachable piece that is separate from the lancet 121. Since both the lancet 121 and the reservoir attachment 120 are disposable items, it will be understood that the reservoir attachment 120 can be made integral with the lancet, wherein separation of the two components would not be possible.

Figure 9D:
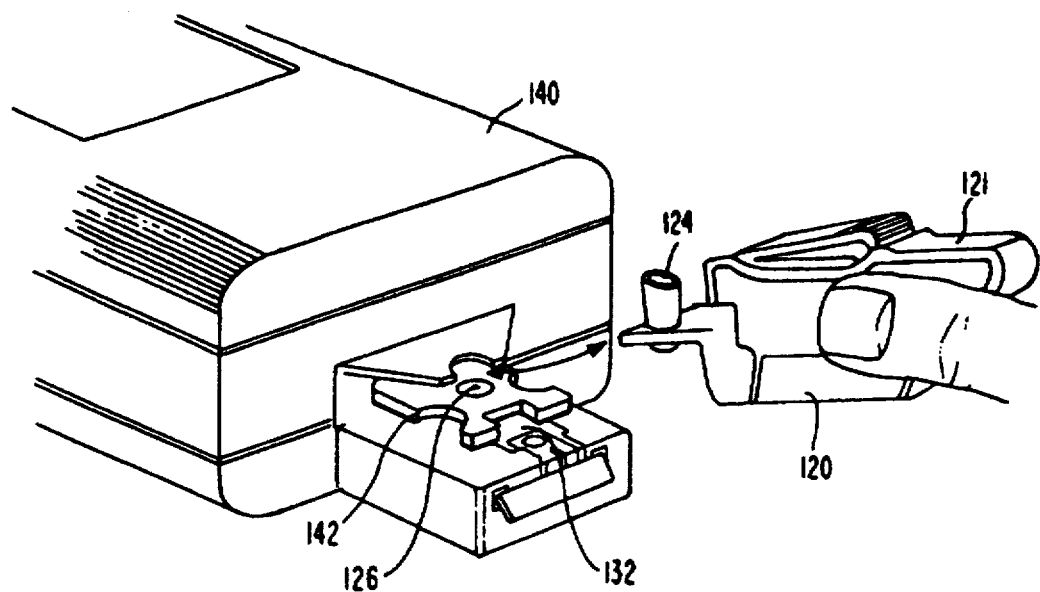
FIGS. 9d and 9e show the lancet and blood collection attachment being applied to a testing device.
Figure 9E:
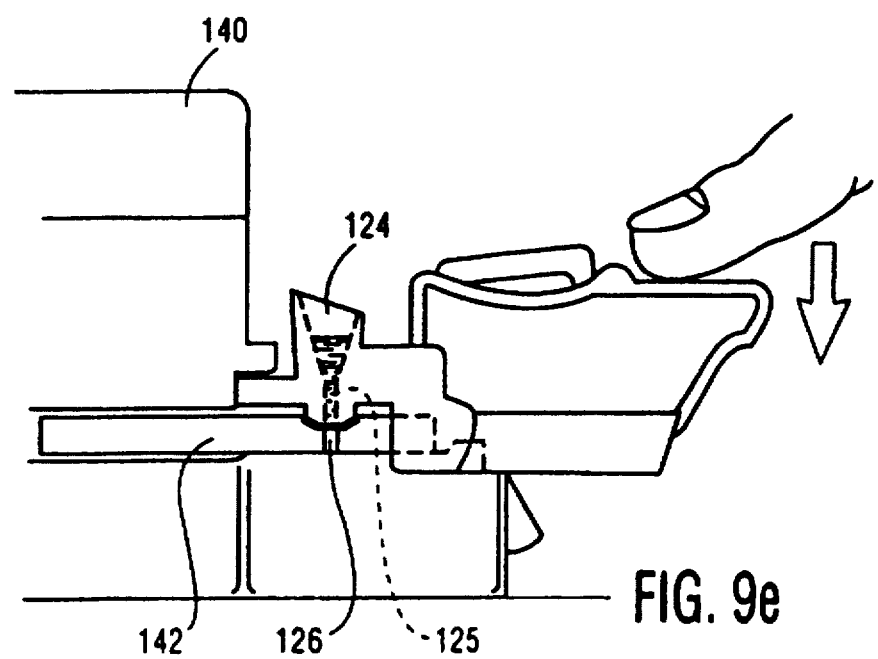
Figure 10:
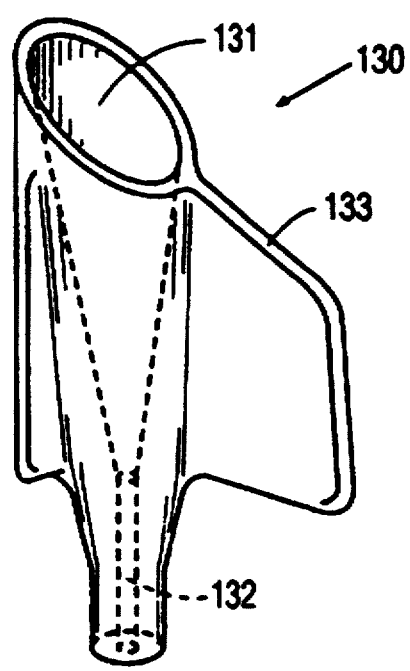
FIG. 10 shows an isolated view of a disposable sample cup.

Referring to FIG. 10 an alternate device for collecting blood is shown. In FIG. 10 a disposable, inexpensive collection cup 130 is shown that can be used in place of the reservoir attachment previously described. The collection cup 130 defines a conical shaped reservoir 131 into which a sample of blood can be placed. A narrow channel 132 extends downwardly from the bottom of the conical shaped reservoir 131, wherein blood is to viscous to flow through the narrow channel 132 unassisted. A handle tab 133 radially extends from the collection cup 130. The handle tab 133 provides a surface that can be readily gripped by a person, whereby the collection cup 130 can be filled with blood and placed in a testing device. The collection cup 130 is filled with a blood sample and placed over a cuvette in a testing machine, such as is shown in FIG. 9d. The collection cup 130 is manipulated so that the narrow channel 132 aligns over the aperture in the cuvette, whereby the blood can be drawn from the collection cup by creating a negative pressure in the cuvette 142.

Figure 11:
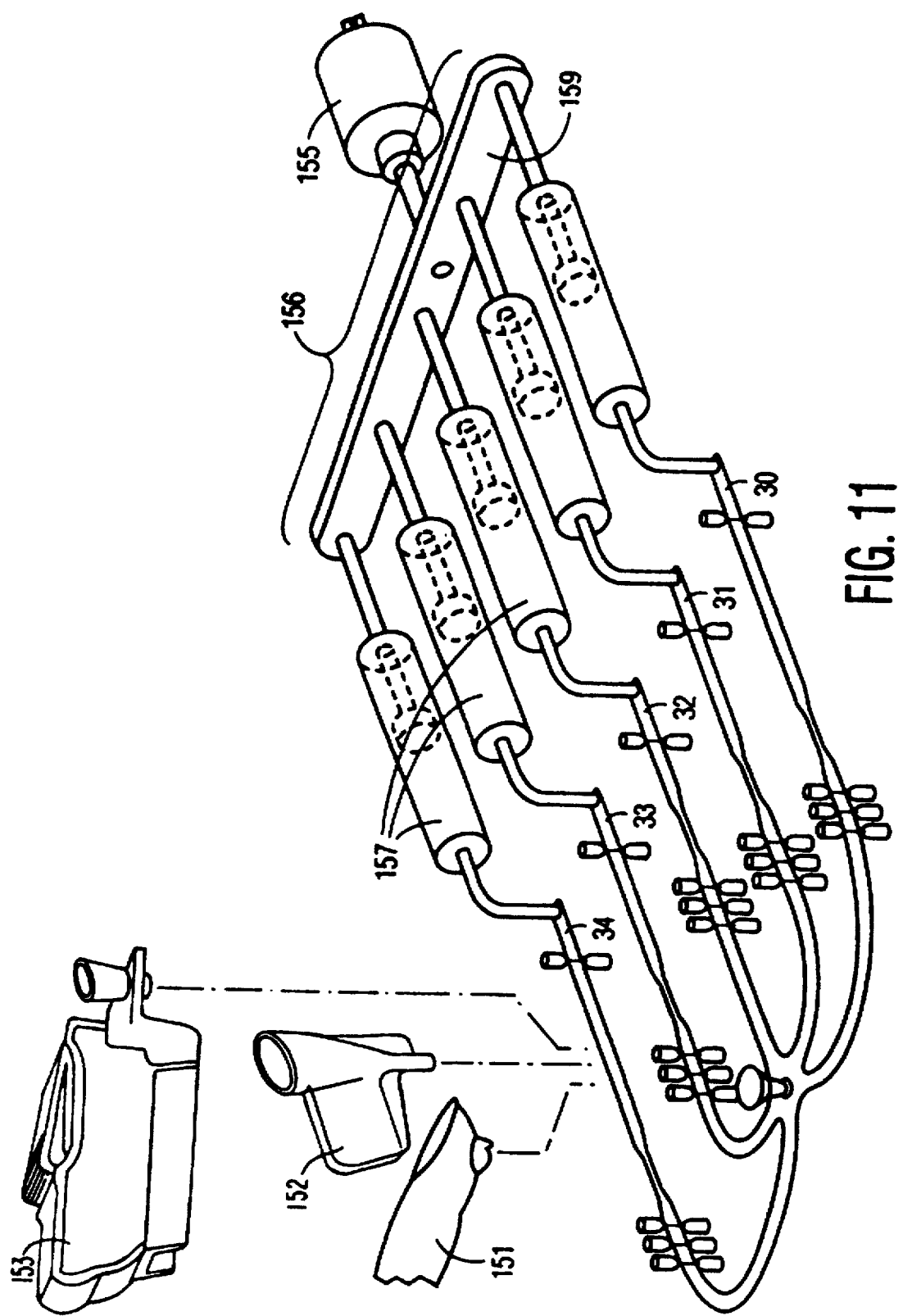
FIG. 11 shows a perspective view of the pneumatic system of the testing device.

Referring to FIG. 11 it can be seen that regardless of whether blood is introduced into the cuvette supply orifice by finger 151, collection cup 152 or lancet/reservoir assembly 153, the blood sample is drawn into the conduits 30, 31, 32, 33, 34 within the cuvette by the creation of a low pressure condition within the conduits 30, 31, 32, 33, 34. Although any pneumatic means can be used to create the low pressure condition, the preferred pneumatic means is a stepped motor 155 and a positive displacement pump array 156. The positive displacement pump array 156 consists of five pump pistons 157, wherein a different pump piston 157 is coupled to each of the conduits 30, 31, 32, 33, 34 in the cuvette. Each of the five pump pistons 157 is driven by a ganged drive 159 that is displaced by the motor 155. As a result, the change in pressure is the same in each of the five conduits 30, 31, 32, 33, 34 as the motor 155 moves the ganged drive 159.

It should be understood that the embodiment described herein is merely exemplary and that a person skilled in the art may make many variations and modifications to the described embodiment utilizing functionally equivalent components to those described. More specifically, it should be understood that any shaped and constructed conduit path can be used in reciprocally cycling the blood test sample. As such, the placement of photoelectric sensors and the time differential between cycles needed to determine coagulation may vary. One may utilize only one photosensor to detect the presence of clotted blood. As one can ascertain, upon the formation of a clot, blood would not move through the constricted area and hence the sensor would not change state. The composition of the normalizing reagent, abnormal reagent and control agent can also be modified utilizing equivalent chemical compounds. All such equivalent components, variations and modifications are intended to be included within the scope of this invention as defined by the appended claims.

What is claimed is:

1. A blood sampling device for providing a blood sample in combination with a cuvette for receiving and performing a blood coagulation test on said blood sample, the combination therewith comprising:

a lancet for creating an incision in a patient's skin that causes the patient to bleed;

a receptacle assembly coupled to said lancet, said receptacle assembly having a receptacle member for receiving a predetermined volume of blood from the patient therein and a receptacle attachment member for coupling said receptacle assembly to said lancet, said receptacle member having a conical-shaped reservoir member extending up from an unitary with a surface of said receptacle attachment member, said conical-shaped reservoir including a first opening through which blood can enter said receptacle member and a second opening through which said blood sample can be drawn from said receptacle member, a cuvette comprising a transparent member having a plurality of conduits for receiving and performing said blood coagulation test on said blood sample and, a channel common to said plurality on conduits through which said predetermined volume of the blood sample can be drawn from said second opening of said receptacle member into each of said conduits, of said cuvette, a first compound contained within a first of said conduits, wherein said first compound reacts with the blood sample within the first of said conduits to produce a first coagulation characteristic, and a second compound contained within a second of said conduits, wherein said second compound reacts with the blood sample within the second of said conduits to produce a second coagulation characteristic.

2. The device according to claim 1, wherein said receptacle assembly and said lancet are disposable.

3. The device according to claim 2, wherein said receptacle assembly is removably attached to said lancet.

4. The device according to claim 2, wherein said receptacle assembly is unitary with said lancet.

5. The device according to claim 1, wherein said receptacle attachment member is unitary with said lancet device.

6. The device according to claim 1, wherein said first opening is substantially larger than said second opening.

* * * * *